US012409275B2

(12) United States Patent
Hourmand et al.

(10) Patent No.: US 12,409,275 B2
(45) Date of Patent: Sep. 9, 2025

(54) AUTO-INJECTOR

(71) Applicant: Sanofi-Aventis Deutschland GMBH, Frankfurt am Main (DE)

(72) Inventors: Yannick Hourmand, Haslingfield (GB); Timothy Donald Barrow-Williams, Herts (GB); Matthew Ekman, Cheshire (GB)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 0 days.

(21) Appl. No.: 19/024,657

(22) Filed: Jan. 16, 2025

(65) Prior Publication Data

US 2025/0152825 A1 May 15, 2025

Related U.S. Application Data

(63) Continuation of application No. 18/498,416, filed on Oct. 31, 2023, which is a continuation of application (Continued)

(30) Foreign Application Priority Data

Dec. 21, 2010 (EP) .................................... 10196067

(51) Int. Cl.
*A61M 5/20* (2006.01)
*A61M 5/50* (2006.01)
*A61M 5/32* (2006.01)

(52) U.S. Cl.
CPC ............ *A61M 5/2033* (2013.01); *A61M 5/50* (2013.01); *A61M 2005/206* (2013.01); *A61M 2005/208* (2013.01); *A61M 5/326* (2013.01)

(58) Field of Classification Search
CPC ...... A61M 2005/206; A61M 2005/208; A61M 5/2033; A61M 5/326; A61M 5/50;

(Continued)

(56) References Cited

U.S. PATENT DOCUMENTS 3,712,301 A 1/1973 Sarnoff
4,964,866 A 10/1990 Szwarc (Continued)

FOREIGN PATENT DOCUMENTS

DE 19819409 A1 11/1999
DE 202004016787 U1 2/2005

(Continued)

OTHER PUBLICATIONS

International Preliminary Report on Patentability in International Appln. No. PCT/EP2011/073502, dated Jun. 25, 2013, 7 pages.

(Continued)

*Primary Examiner* — William R Carpenter
(74) *Attorney, Agent, or Firm* — Fish & Richardson P.C.

(57) ABSTRACT

According to the invention, an auto-injector for administering a dose of a liquid medicament (M) comprises of a substantially cylindrical housing arranged to contain a pre-filled syringe filled with the medicament (M), a needle shroud slidably arranged with respect to the housing and adapted to rest on the skin of a patient receiving an injection, a releasable drive means arranged within the housing that is capable of, upon release, translating the needle shroud in a proximal direction (P) towards a safe position (PS) and a rotating collar rotatably arranged within the housing. The needle shroud in the safe position (PS) surrounds the injection needle after the injection has been carried out. The rotating collar engages the needle shroud in a manner that forces the rotating collar to rotate within the housing when the needle shroud is translated in the proximal direction (P).

30 Claims, 5 Drawing Sheets

PA 13 3.2 3 1 2.2 4.1 2.3 2 9 6.1 3 8 S 2.6 7.2 9.2 P M L D 12 14 4 11 5 10 9.1 I 6 7 17

Related U.S. Application Data

No. 16/909,107, filed on Jun. 23, 2020, now Pat. No. 11,833,331, which is a continuation of application No. 15/669,571, filed on Aug. 4, 2017, now Pat. No. 10,729,853, which is a continuation of application No. 13/993,528, filed as application No. PCT/EP2011/073502 on Dec. 21, 2011, now Pat. No. 9,724,472.

(60) Provisional application No. 61/432,255, filed on Jan. 13, 2011.

(58) Field of Classification Search
CPC .. A61M 2005/3261; A61M 2005/3263; A61M 2005/3264; A61M 2005/3265; A61M 2005/3267; A61M 2005/326
See application file for complete search history.

(56) References Cited

U.S. PATENT DOCUMENTS 5,478,316 A 12/1995 Bitdinger et al.
5,480,387 A 1/1996 Gabriel et al.
5,559,309 A 9/1996 Zabler et al.
5,599,309 A 2/1997 Marshall et al.
6,004,297 A 12/1999 Steenfeldt-Jensen et al.
6,277,099 B1 8/2001 Strowe et al.
6,371,939 B2 4/2002 Bergens et al.
6,454,743 B1 9/2002 Weber
6,620,137 B2 9/2003 Kirchhofer et al.
6,743,205 B2 6/2004 Nolan, Jr. et al.
7,195,616 B2 3/2007 Diller et al.
7,291,132 B2 11/2007 DeRuntz et al.
7,297,135 B2 11/2007 Jeffrey
7,341,575 B2 3/2008 Rice et al.
7,597,685 B2 10/2009 Olson
7,678,085 B2 3/2010 Graf
7,717,877 B2 5/2010 Lavi et al.
7,771,398 B2 8/2010 Knight et al.
7,918,824 B2 4/2011 Bishop et al.
7,976,494 B2 7/2011 Kohlbrenner et al.
8,038,649 B2 10/2011 Kronestedt
8,048,037 B2 11/2011 Kohlbrenner et al.
8,062,255 B2 11/2011 Brunnberg et al.
8,083,711 B2 12/2011 Enggaard
8,313,465 B2 11/2012 Harrison
8,323,238 B2 12/2012 Cronenberg et al.
8,357,125 B2 1/2013 Grunhut et al.
8,361,025 B2 1/2013 Lawlis et al.
8,366,680 B2 2/2013 Raab
8,376,993 B2 2/2013 Cox et al.
8,376,997 B2 2/2013 Hogdahl et al.
8,403,883 B2 3/2013 Fayyaz et al.
8,409,138 B2 4/2013 James et al.
8,409,141 B2 4/2013 Johansen et al.
8,409,148 B2 4/2013 Fiechter et al.
8,439,864 B2 5/2013 Galbraith et al.
8,491,538 B2 7/2013 Kohlbrenner et al.
8,568,359 B2 10/2013 Carrel et al.
8,617,109 B2 12/2013 Kronestedt et al.
8,617,124 B2 12/2013 Wieselblad et al.
8,632,507 B2 1/2014 Bartha
8,647,299 B2 2/2014 Stamp
8,684,969 B2 4/2014 Moller et al.
8,708,973 B2 4/2014 Holmqvist
8,734,394 B2 5/2014 Admas et al.
8,734,402 B2 5/2014 Sharp et al.
8,758,292 B2 6/2014 Tschirren et al.
8,808,250 B2 8/2014 Ekman et al.
8,808,251 B2 8/2014 Raab et al.
8,821,451 B2 9/2014 Daniel
8,834,431 B2 9/2014 Kohlbrenner et al.
8,840,591 B2 9/2014 Raab et al.
8,882,723 B2 11/2014 Smith et al.
8,911,411 B2 12/2014 Nielsen
8,939,934 B2 1/2015 Brereton et al.
8,945,063 B2 2/2015 Wotton et al.
8,956,331 B2 2/2015 Johansen et al.
8,961,473 B2 2/2015 Heald
8,968,256 B2 3/2015 Raab
8,968,258 B2 3/2015 Nzike et al.
8,992,484 B2 3/2015 Radmer et al.
8,992,487 B2 3/2015 Eich et al.
9,005,160 B2 4/2015 Karlsson et al.
9,011,386 B2 4/2015 Kronestedt et al.
9,011,387 B2 4/2015 Ekman et al.
9,022,991 B1 5/2015 Moeller
9,022,994 B2 5/2015 Moser et al.
9,044,548 B2 6/2015 Miller et al.
9,044,553 B2 6/2015 James et al.
9,057,369 B2 6/2015 Kohlbrenner et al.
9,061,104 B2 6/2015 Daniel
9,067,024 B2 6/2015 Roberts et al.
9,089,652 B2 7/2015 Nzike et al.
9,108,002 B2 8/2015 Markussen
9,125,988 B2 9/2015 Karlsson
9,132,235 B2 9/2015 Holmqvist
9,199,038 B2 12/2015 Daniel
9,205,199 B2 12/2015 Kemp et al.
9,216,256 B2 12/2015 Olson et al.
9,233,213 B2 1/2016 Olson et al.
9,233,214 B2 1/2016 Kemp et al.
9,233,215 B2 1/2016 Hourmand et al.
9,242,044 B2 1/2016 Markussen
9,272,098 B2 3/2016 Hourmand et al.
9,283,326 B2 3/2016 Kemp et al.
9,283,327 B2 3/2016 Hourmand et al.
9,283,328 B2 3/2016 Dasbach
9,308,327 B2 4/2016 Marshall et al.
9,333,304 B2 5/2016 Brereton et al.
9,339,607 B2 5/2016 Langley et al.
9,352,088 B2 5/2016 Ekman et al.
9,358,345 B2 6/2016 Brereton et al.
9,358,351 B2 6/2016 Ekman et al.
9,393,368 B2 7/2016 Nzike et al.
9,402,957 B2 8/2016 Adams et al.
9,408,976 B2 8/2016 Olson et al.
9,408,977 B2 8/2016 Butler et al.
9,408,979 B2 8/2016 Veasey et al.
9,415,165 B2 8/2016 Cowe
9,421,336 B2 8/2016 Ekman et al.
9,427,525 B2 8/2016 Barrow-Williams et al.
9,446,196 B2 9/2016 Hourmand et al.
9,446,201 B2 9/2016 Holmqvist
9,457,149 B2 10/2016 Kemp et al.
9,457,152 B2 10/2016 Raab et al.
9,492,622 B2 11/2016 Brereton et al.
9,662,452 B2 5/2017 Daniel
9,867,940 B2 1/2018 Holmqvist et al.
9,872,961 B2 1/2018 Fourt et al.
10,118,001 B2 11/2018 Fourt et al.
10,314,981 B2 6/2019 Sampson et al.
10,350,362 B2 7/2019 Dennis, Jr. et al.
10,363,377 B2 7/2019 Atterbury et al.
10,420,898 B2 9/2019 Daniel
10,569,019 B2 2/2020 Hirschel et al.
RE47,903 E 3/2020 Hourmand et al.
10,799,647 B2 10/2020 Hosteettler et al.
RE48,593 E 6/2021 Hourmand et al.
11,298,462 B2 4/2022 Atterburg et al.
11,383,044 B2 7/2022 Tschirren et al.
11,400,217 B2 8/2022 Hourmand et al.
11,452,821 B2 9/2022 Lafever et al.
11,458,252 B2 10/2022 Hourmand et al.
11,471,601 B1 10/2022 Hourmand et al.
11,607,495 B1 3/2023 Hourmand et al.
11,612,691 B2 3/2023 Hourmand et al.
12,329,936 B2 6/2025 Hourmand et al.
12,337,146 B2 6/2025 Hourmand et al.
12,337,147 B2 6/2025 Hourmand et al.
12,337,148 B2 6/2025 Hourmand et al.
2002/0007154 A1 1/2002 Hansen et al.
2002/0095120 A1 7/2002 Larsen et al.
2003/0105430 A1 6/2003 Lavi et al.

(56) References Cited

U.S. PATENT DOCUMENTS

2004/0039336 A1 2/2004 Amark et al.
2005/0101919 A1 5/2005 Brunnberg
2005/0203466 A1 9/2005 Hommann et al.
2005/0222539 A1 10/2005 Gonzales et al.
2006/0153693 A1 7/2006 Fiechter et al.
2006/0224124 A1 10/2006 Scherer
2006/0258990 A1 11/2006 Weber
2006/0270984 A1 11/2006 Hommann
2006/0270985 A1 11/2006 Hommann et al.
2006/0287630 A1 12/2006 Hommann
2007/0027430 A1 2/2007 Hommann
2007/0129686 A1 6/2007 Daily et al.
2008/0262427 A1 10/2008 Hommann
2008/0269692 A1 10/2008 James et al.
2008/0312591 A1 12/2008 Harrison
2009/0012471 A1 1/2009 Harrison
2009/0088688 A1 4/2009 Timothy Donald et al.
2009/0292246 A1 11/2009 Slate et al.
2009/0312705 A1 12/2009 Grunhut et al.
2010/0049125 A1 2/2010 James et al.
2010/0185178 A1 7/2010 Sharp et al.
2010/0256570 A1 10/2010 Maritan
2010/0262083 A1 10/2010 Grunhut et al.
2010/0268170 A1 10/2010 Carrel et al.
2010/0280461 A1 11/2010 Forstreuter
2010/0312195 A1 12/2010 Johansen et al.
2011/0046567 A1 2/2011 Radmer et al.
2011/0270161 A1 11/2011 Harrison et al.
2012/0010575 A1 1/2012 Jones et al.
2012/0041387 A1 2/2012 Bruggemann et al.
2012/0053528 A1 3/2012 Bollenbach et al.
2012/0116319 A1 5/2012 Grunhut
2012/0172817 A1 7/2012 Bruggemann et al.
2013/0035647 A1 2/2013 Veasey et al.
2013/0041328 A1 2/2013 Daniel
2013/0123710 A1 5/2013 Ekman et al.
2013/0261556 A1 10/2013 Jones et al.
2013/0274662 A1 10/2013 Hourmand et al.
2013/0274666 A1 10/2013 Brereton et al.
2013/0274677 A1 10/2013 Ekman et al.
2013/0289525 A1 10/2013 Kemp et al.
2013/0310757 A1 11/2013 Brereton et al.
2013/0345643 A1 12/2013 Hourmand et al.
2015/0273157 A1 10/2015 Kohlbrenner et al.
2016/0089498 A1 3/2016 Daniel
2018/0064875 A1 3/2018 Holmqvist
2019/0374717 A1 12/2019 Swanson et al.
2022/0211947 A1 7/2022 Hourmand et al.
2022/0218906 A1 7/2022 Hourmand et al.
2022/0313915 A1 10/2022 Hourmand et al.
2023/0019806 A1 1/2023 Hourmand et al.
2023/0086760 A1 3/2023 Hourmand et al.
2024/0207520 A1 6/2024 Hourmand et al.
2024/0238521 A1 7/2024 Hourmand et al.
2024/0238522 A1 7/2024 Hourmand et al.
2024/0238523 A1 7/2024 Hourmand et al.
2025/0152826 A1 5/2025 Hourmand et al.
2025/0152827 A1 5/2025 Hourmand et al.
2025/0152828 A1 5/2025 Hourmand et al.

FOREIGN PATENT DOCUMENTS

DE 102004060146 A1 8/2005
DE 202007000578 U1 3/2007
DE 102005052502 A1 5/2007
EP 0666084 A2 8/1995
EP 0824923 A1 2/1998
EP 0991441 A1 12/2003
EP 2399634 A1 12/2011
EP 2468334 A1 6/2012
EP 2468335 A1 6/2012
GB 2438592 A 12/2007
JP 2001-521792 A 11/2001
JP 2002-528182 A 9/2002
JP 2008-521482 A 9/2008
JP 2010-520786 A 6/2010
JP 2010-540059 A 12/2010
WO WO 1999/022790 A1 5/1999
WO WO 1999/022792 A1 5/1999
WO WO 1999/053979 A1 10/1999
WO WO 2000/024441 A1 5/2000
WO WO 2002/047746 A1 6/2002
WO WO 2003/062672 A1 7/2003
WO WO 2005/044345 A1 5/2005
WO WO 2005/097238 A2 10/2005
WO WO 2005/115507 A1 12/2005
WO WO 2006/057604 A1 6/2006
WO WO 2006/111861 A2 10/2006
WO WO 2007/083115 A1 7/2007
WO WO 2007/099044 A1 9/2007
WO WO 2007/129324 A2 11/2007
WO WO 2008/059385 A2 5/2008
WO WO 2008/112472 A2 9/2008
WO WO 2008/116688 A1 10/2008
WO WO 2009/040602 A1 4/2009
WO WO 2009/040607 A1 4/2009
WO WO 2009/040672 A2 4/2009
WO WO 2009/062508 A1 5/2009
WO WO 2010/035060 A1 4/2010
WO WO 2010/063707 A1 6/2010
WO WO 2010/136077 A1 12/2010
WO WO 2011/012903 A1 2/2011
WO WO 2011/109205 A2 9/2011
WO WO 2011/111006 A2 9/2011
WO WO 2011/117592 A1 9/2011
WO WO 2011/126439 A1 10/2011
WO WO 2012/045350 A1 4/2012
WO WO 2012/085021 A1 6/2012
WO WO 2012/085024 A2 6/2012
WO WO 2019/074788 A1 4/2019
WO WO 2020/190529 A1 9/2020
WO WO 2021/008839 A1 1/2021

OTHER PUBLICATIONS

International Search Report and Written Opinion in International Appln. No. PCT/EP2011/073502, dated Mar. 19, 2012, 9 pages.

AUTO-INJECTOR

CROSS REFERENCE TO RELATED APPLICATIONS

The present application is a continuation of U.S. patent application Ser. No. 18/498,416, filed Oct. 31, 2023, which is a continuation of U.S. patent application Ser. No. 16/909,107, filed Jun. 23, 2020, now U.S. Pat. No. 11,833,331, which is a continuation of U.S. patent application Ser. No. 15/669,571, filed Aug. 4, 2017, now U.S. Pat. No. 10,729,853, which is a continuation of U.S. patent application Ser. No. 13/993,528, with a 371 filing date of Jun. 12, 2013, now U.S. Pat. No. 9,724,472, which is a U.S. National Phase Application pursuant to 35 U.S.C. § 371 of International Application No. PCT/EP2011/073502, filed Dec. 21, 2011, which claims priority to European Patent Application No. 10196067.2, filed Dec. 21, 2010, and U.S. Provisional Patent Application No. 61/432,255, filed Jan. 13, 2011. The entire disclosure contents of these applications are herewith incorporated by reference into the present application.

TECHNICAL FIELD

The invention relates to an auto-injector for administering a dose of a liquid medicament.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

SUMMARY

It is an object of the present invention to provide an improved auto-injector.

The object is achieved by an auto-injector according to claim 1.

Preferred embodiments of the invention are given in the dependent claims.

In the context of this specification, the terms distal and proximal are defined from the point of view of a person receiving an injection. Consequently, a proximal direction refers to a direction pointing towards the body of a patient receiving the injection and a proximal end defines an end of an element that is directed towards the body of the patient. Respectively, the distal end of an element or the distal direction is directed away from the body of the patient receiving the injection and opposite to the proximal end or proximal direction.

According to the invention, an auto-injector for administering a dose of a liquid medicament comprises

- a substantially cylindrical housing arranged to contain a pre-filled syringe filled with the medicament,
- a needle shroud slidably arranged with respect to the housing and adapted to rest on the skin of a patient receiving an injection,
- a releasable drive means arranged within the housing that is capable of, upon release, translating the needle shroud in a proximal direction towards a safe position and
- a rotating collar rotatably arranged within the housing. The needle shroud in the safe position surrounds the injection needle after the injection has been carried out. The rotating collar engages the needle shroud in a manner that forces the rotating collar to rotate within the housing when the needle shroud is translated in the proximal direction.

A stopper may be arranged in the syringe barrel arranged to seal its distal end and to expel the dose of medicament. A coupling shroud may be slidably arranged within the housing and releasably coupled to a plunger that is connected to the stopper. The drive means may be arranged between a distal end of the housing and the coupling shroud to bias the coupling shroud in a proximal direction towards the skin of a patient receiving an injection.

The rotating collar creates friction to slow down a proximal movement of the needle shroud that rests on the skin of the patient during the injection. The rotating collar acts as a dampening element that alleviates the pressure exerted upon the skin of the patient by the needle shroud that is driven by the drive means. Thus, the risk of injuries is reduced and, in particular, bruises may be avoided. Furthermore, the modulus of resilience of the single drive means may be chosen to be sufficiently large without having to worry about potential injury risks. Thus, the modulus of resilience of the drive means is adapted to reliably provide an energy supply for executing a plurality of actions comprising, among others, the advancing and releasing of the needle shroud, the displacement of the stopper to expel the medicament and the decoupling of the plunger and the coupling shroud.

Preferably, the rotating collar comprises a pin that engages a helical recess formed into the needle shroud. The engagement of the helical recess and the pin forces the rotating collar to rotate around the needle shroud when the needle shroud is translated. This dampens the proximal movement of the needle shroud and thus reduces the pressure exerted upon the skin of the patient by generating friction.

According to a possible embodiment of the invention, the needle shroud is slidable in a distal direction from an advanced position to a retracted position. In particular, the needle shroud may be slid to the retracted position by placing the auto-injector onto the skin of the patient receiving the injection and pressing the needle shroud against the skin of the patient. The needle shroud in the retracted position indicates the correct placement of the auto-injector. An activation of a mechanism of the auto-injector delivering the medicament to the patient requires the needle shroud to be positioned in the retracted position to ensure that the auto-injector is properly used. The needle shroud is slidable in the proximal direction from the retracted position to the safe position, wherein the needle shroud surrounds an injection needle of the pre-filled syringe to prevent accidental needle stick injuries after the injection has been carried out.

According to another possible embodiment of the invention, the drive means is arranged to be released by manual actuation of a release element that is hinged to a lateral side of the housing. Conventional auto-injectors are commonly activated by actuating a push button or the like arranged at a distal end of the auto-injector. An inexperienced user of such a conventional auto-injector may easily mistake the distal end for a proximal end of the auto-injector and thus may pierce his finger while trying to actuate the auto-injector. The lateral arrangement of the release element is a simple means to prevent such accidental needle stick injuries resulting from a misuse of the auto-injector.

Alternatively, the release element is in slidable arrangement with the housing and may be translated with respect to the housing in the proximal direction to release the drive means. The auto-injector according to this embodiment of the invention is particularly intuitive to operate.

According to another possible embodiment of the invention, the auto-injector comprises safety means that cooperate with the needle shroud that is arranged to prevent a release of the drive means when the needle shroud is in the advanced position and hence is not pushed against the skin of the patient. This mechanism avoids an early release of the drive means and thus a premature expelling of the medicament. Furthermore, injuries resulting from an activation of the drive means when the auto-injector is not placed, or not properly placed onto the skin of the patient are reduced.

The safety means may comprise a blocking element slidably arranged relative to the housing. The blocking element is arranged to limit a pivoting movement of the release element hinged to the lateral side of the housing when the needle shroud is in the advanced position. A release of the drive means is thus prevented. The release element is allowed to pivot about the hinge when the needle shroud is moved to the retracted position by pressing the needle shroud against the skin surface of the patient receiving the injection.

In one possible embodiment of the invention, the safety means comprises an elastic bushing that engages a plunger of the pre-filled syringe and/or a coupling shroud that is biased by the drive means and coupled to the plunger of the pre-filled syringe. The elastic bushing is firmly attached to a proximal end of the housing and may engage the coupling shroud and/or the plunger to prevent an inadvertent release of the drive means.

In another preferred embodiment of the invention, the drive means is capable of, upon release, driving the coupling shroud releasably coupled to the plunger from a first position in the proximal direction. The coupling shroud is driven by the drive means to interact with different components of the auto-injector, so that the resilient force provided by the drive means may be used to power a variety of functions of the auto-injector. The proximal translatory movement of the coupling shroud with respect to the housing

- translates a syringe retainer receiving the pre-filled syringe in the proximal direction to expose the injection needle of the pre-filled syringe,
- depresses the plunger connected to a stopper into the syringe barrel to expel the dose of medicament and
- translates the needle shroud in the proximal direction. The coupling shroud mediates the resilient force provided by the drive means to this variety of different components of the auto-injector and thus allows for a compact design of the auto-injector. In particular, the auto-injector may be powered by just a single drive means to accomplish a plurality of tasks necessary for safely carrying out the injection.

According to yet another possible embodiment of the invention, the syringe retainer is releasably mounted to the housing. The needle shroud in the retracted position releases the syringe retainer to allow for the proximal translation of the syringe retainer with respect to the housing. Thus, a proximal movement of the syringe retainer that in particular inserts the injection needle into the skin of the patient is prevented until the auto-injector is correctly placed upon the skin of the patient and the needle shroud is pushed against the skin surface towards the retracted position. This prevents an inadvertent early release of the drive means.

The coupling shroud is initially in a first position, and coupled to the plunger to translate the syringe retainer proximally, whereby the injection needle is inserted into the skin of the patient, and to depress the stopper into the syringe barrel to expel the medicament. The plunger and the coupling shroud are decoupled from each other at the proper pre-determined second position after the medicament has been completely or partially delivered. The pre-determined second position is defined by a longitudinal aperture in the housing.

According to another possible embodiment of the invention, a coupling catch is arranged to abut against a shoulder formed to the plunger as a particularly simple and reliable means to releasably couple the plunger to the coupling shroud. The coupling shroud is moved by the action of the relaxing drive means in the proximal direction and is coupled to the plunger connected to the stopper to insert the injection needle before the injection and to expel the medication during the injection.

The aperture formed into the lateral side of the housing at the second position allows the coupling catch to deflect radially outwards at the second position, so that the coupling shroud is decoupled from the plunger after the medicament is partially or completely delivered.

Preferably, the drive means is arranged as a single compression spring. The mechanism of the auto-injector is arranged in a manner that a plurality of functions is executed by the single drive means. The injection needle is inserted into the skin of the patient, the plunger is translated to expel the medicament and the needle shroud is moved proximally to provide needle safety after the injection is completed by the action of the spring means. Conventional auto-injectors usually comprise a plurality of spring means to accomplish these tasks. The auto-injector according to the invention comprises only few parts and is particularly inexpensive to mass-produce. Consequently, the auto-injector is particularly suited as a single-use device that may be disposed after an injection has been carried out.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
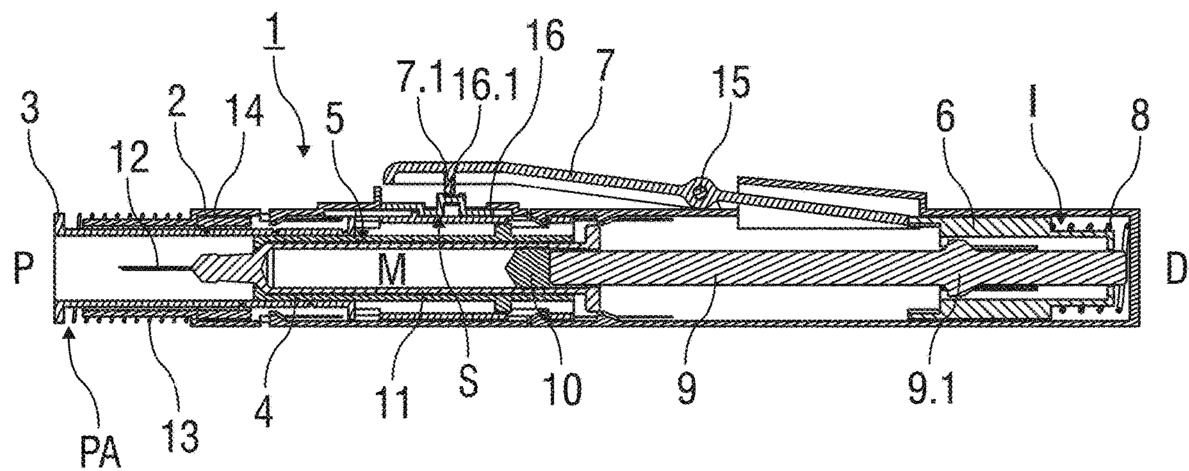
FIGS. 1A und 1B show two different sectional views of an auto-injector according to a first embodiment of the invention with a hinged release element before an injection.
Figure 1B:
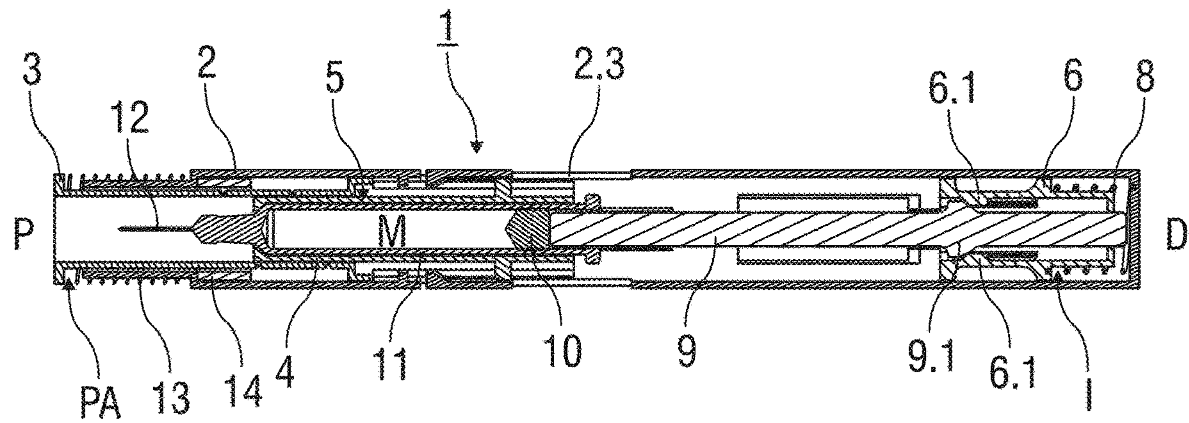

FIGS. 1A and 1B show two sectional views of an essentially cylindrical auto injector 1 according to a first embodiment of the invention, wherein the sectional plane shown in FIG. 1A is oriented perpendicularly to the one shown in FIG. 1B. The auto-injector 1 comprises a housing 2, a proximal needle shroud or sleeve 3, a syringe retainer 4 adapted to mount and move translatably with a pre-filled syringe 5 within the housing 2, a coupling/decoupling shroud or member 6 slidably arranged within the housing 2 and a release element 7 hinged to a lateral side of the substantially cylindrical housing 2 of the auto-injector 1.

A single drive means 8 is arranged between the distal end of the housing 2 and the coupling shroud 6 to bias the coupling shroud 6 in a proximal direction P towards the skin of a patient receiving an injection.

According to one possible embodiment of the invention, the drive means 8 is arranged as a single, conventional compression spring.

The coupling shroud 6 is releasably coupled to a plunger 9 that is connected to a stopper 10 fluid-tightly sealing a distal end of a syringe barrel 11 containing a dose of a medicament M. An inner cavity of the syringe barrel 11 is in fluid communication with an injection needle 12, so that the dose of the medicament M may be expelled through the injection needle 12 by displacing the stopper 10 in the proximal direction P.

Before the injection, the coupling shroud 6 abuts against a distal end of the release element 7 to releasably retain the coupling shroud 6 in a first position I, wherein the coupling shroud 7 is located at a distal end of the housing 2. The drive means 8 is compressed, so that the coupling shroud 6 is strongly biased in the proximal direction P.

The plunger 9 extends from the syringe barrel 11 in a distal direction D and comprises a shoulder 9.1 of increased diameter. The coupling shroud 6 comprises an inwardly protruding coupling catch 6.1 that bears against the shoulder 9.1 so that the plunger 9 and the coupling shroud 6 may be jointly moved in the proximal direction P by the action of the relaxing drive means 8.

The proximal end of the needle shroud 3 is designed to be pushed against the skin surface of the patient during the injection. Edges of the needle shroud 3 may thus be smoothed to avoid injuries. The needle shroud 3 is slidably arranged within the housing 2 of the auto-injector 1, so that the needle shroud 3 may be pushed from an advanced position PA shown in FIGS. 1A and 1B in the distal direction D. A biasing means 13 bears against the needle shroud 3 and the housing 2 to bias the needle shroud 3 towards the advanced position PA.

An annular rotating collar 14 engages an outer surface of the needle shroud 3. The rotating collar 14 rotates around an axis of the substantially cylindrical auto-injector 1 when the needle shroud 3 is longitudinally displaced in the proximal and/or the distal direction P, D. The rotating collar 14 acts as a damping means that creates friction to slow down the movement of the needle shroud 3 and to reduce the pressure exerted onto the skin of the patient receiving the injection.

The release element 7 hinged to the housing 2 works like a see-saw: a proximal section may be pushed radially inwards, whereby the release element 7 pivots about a hinge

15, so that the distal section of the release element 7 moves radially outwards and the coupling shroud 6 is disengaged to release the drive means 8.

The auto-injector 1 comprises safety means S that prevent an early release of the drive means 8. The safety means S ensure that the needle shroud 3 is pushed against the skin of the person receiving the injection before the drive means 8 may be released.

According to the first embodiment of the invention, the safety means S comprise a blocking element 16 slidably arranged with the housing 2. When the needle shroud 3 is positioned in the advanced position PA, the blocking element 16 is positioned to prevent a pivoting movement of the release element 7 and thus a release of the coupling shroud 6. A radially outwards protruding blocking projection 16.1 of the blocking element 16 is located opposite to an inward protrusion 7.1 formed to the release element 7. If the proximal section of the release element 7 is pushed inwards, the inward protrusion 7.1 abuts against the blocking projection 16.1 to limit the pivoting movement of the release element 7, so that a release of the coupling shroud 6 and the drive means 8 is prevented.

Figure 2:
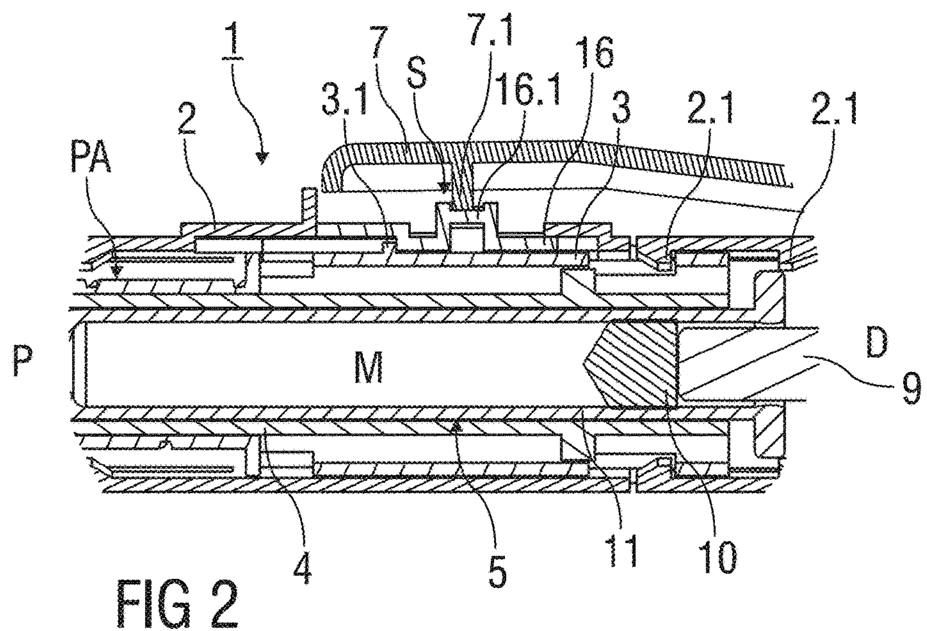
FIG. 2 is an expanded sectional view of the auto-injector according to the first embodiment, wherein the release element is blocked to prevent an inadvertent release of a drive means.

FIG. 2 shows a proximal section of the auto-injector 1 in a sectional view with the blocking element 16 positioned to prevent an inadvertent actuation of the hinged release element 7 to release the drive means 8.

A distal end of the needle shroud 3 is clipped to the housing 2 and retained between two inwardly protruding retaining protrusions 2.1 formed into an inner surface of the housing 2. The two retaining protrusions 2.1 are longitudinally displaced from each other to limit the range of axial displacement of the needle shroud 3 with respect to the housing 2. A boss 3.1 formed into an outer surface of the needle shroud 3 bears against an inner surface of the blocking element 16, so that the blocking element 16 may move with the needle shroud 3 in the proximal direction P to deblock the release element 7.

Figure 3:
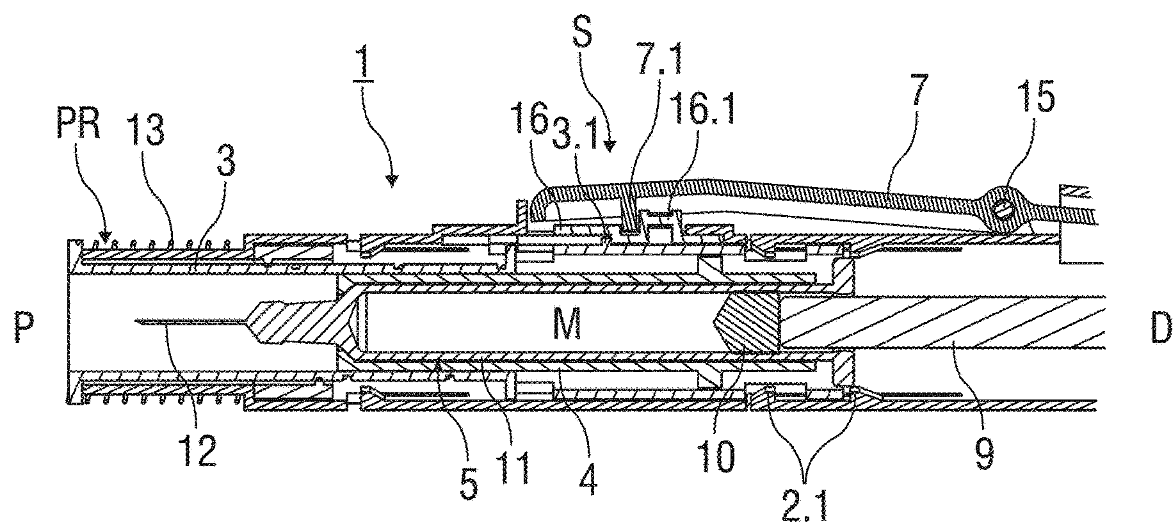
FIG. 3 is an expanded sectional view of the hinged release element that is actuated to release the drive means.

The blocking projection 16.1 comprises a central indentation that forces a user of the auto-injector 1 to perform a sequence of actions necessary to inject the dose of the medicament M in the proper order. If the release element 7 is pushed inwards before the needle shroud 3 is moved proximally from the advanced position PA towards a retracted position PR (see FIG. 3) by pushing the needle shroud 3 towards the skin of the patient, the inward projection 7.1 is retained in the central indentation of the blocking projection 16.1, so that both the longitudinal displacement of the needle shroud 3 and the pivoting movement of the release element 7 is blocked.

A proper sequence of actions for injecting the dose of the medicament M is described in the following. First, the user pushes the needle shroud 3 against the skin to move the needle shroud 3 distally to the retracted position PR illustrated in FIG. 3. The blocking element 16 jointly moves with the needle shroud 3 in the distal direction D, so that the release element 7 may be manually actuated to pivot about the hinge 15, whereby the drive means 8 are released.

Upon release of the drive means 8, the coupling shroud 6 is urged in the proximal direction P. The single and fully compressed drive means 8 drives the coupling shroud 6 and the plunger 9 coupled thereto in the proximal direction P. The coupling shroud 6 first pushes the syringe retainer 4 by means of plunger 9, stopper 10 and the friction between stopper 10 and syringe 11 proximally to insert the injection needle 12 into the skin of the patient and a first clip connection 2.2 formed into a lateral side of the housing 2 latches to an outward protrusion 4.1 of the syringe retainer 4, as illustrated in more detail in FIG. 4B.

The syringe retainer 4 and the pre-filled syringe 5 mounted thereto is now locked to the housing 2. The coupling shroud 6 is moved further in the proximal direction P by the action of the relaxing drive means 8, whereby the plunger 9 is depressed into the syringe barrel 11 to expel the dose of the medicament M contained therein through the injection needle 12.

Figure 4A:
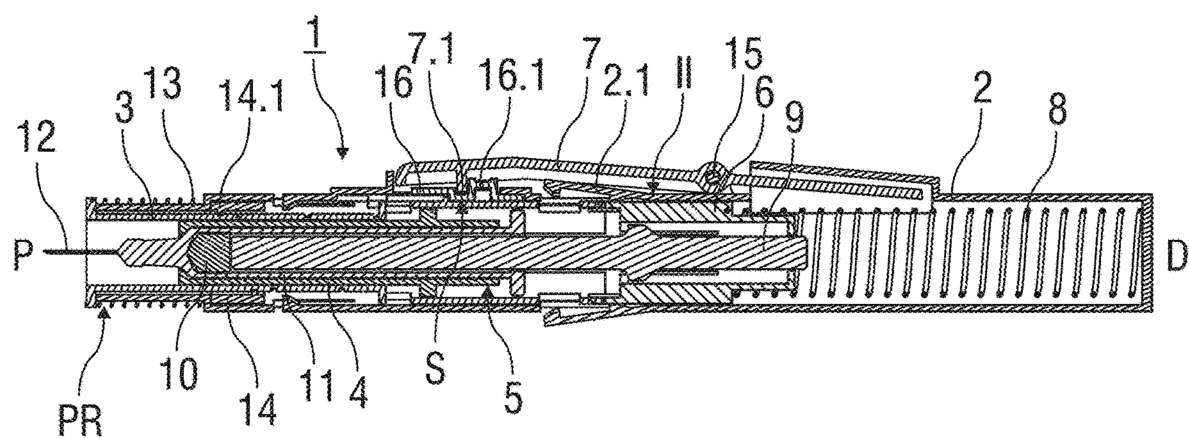
FIGS. 4A and 4B are two different sectional views of the auto-injector according to the first embodiment after a drug has been delivered.
Figure 4B:
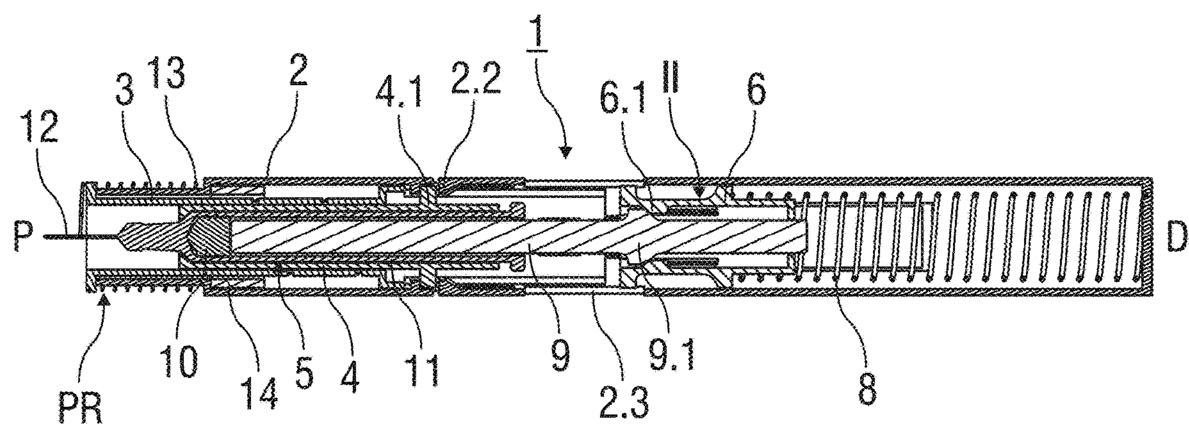

FIGS. 4A and 4B show two sectional views of the auto-injector 1 according to the first embodiment of the invention with the plunger 9 fully depressed within the syringe barrel 11. The dose of the medicament M has been delivered beneath the skin of the patient. The coupling shroud 6 is located in an intermediate second position II. The drive means 8 is not yet completely discharged and biases the coupling shroud 6 in the proximal direction P. The shoulder 9.1 engages a ramp of the coupling catch 6.1 to deflect the coupling catch 6.1 in a radial outward direction. An aperture 2.3 is formed into the housing 2 to allow for a radial outward deflection of the coupling catch 6.1, so that the coupling catch 6.1 overcomes the shoulder 9.1 decoupling the coupling shroud 6 from the plunger 9.

In a possible embodiment of the invention, the aperture 2.3 defining the second position II is located at a longitudinal position along the housing 2 that allows for a full depression of the plunger 9 completely emptying the syringe barrel 11 before the plunger 9 is decoupled from the coupling shroud 6.

Alternatively, the aperture 2.3 defining the second position II may be located at a longitudinal position along the housing 2 that allows for an adjustment space accounting for manufacturing tolerances. The adjustment space is dimensioned as to allow for a reliable decoupling of the plunger 9 from the coupling shroud 6 even if the parts constituting the auto-injector 1 comprise mismatch in mould or are slightly misaligned. In this alternative embodiment, the dose of the medicament M may or may not be completely expelled before the plunger 9 is decoupled from the coupling shroud 6.

The retaining protrusions 2.1 are elastically supported and may be deflected radially outwards to release the needle shroud 3. The coupling shroud 6 engages a ramp of the retaining protrusions 2.1 and splays the retaining protrusions 2.1 outwards, whereby the needle shroud 3 is released and allowed to move proximally from the retracted position PR towards an extended safe position PS.

The drive means 8 is still partially loaded when the coupling shroud 6 is located in the second position II. In a possible embodiment of the invention the biasing force of the drive means 8 exerted on the coupling shroud 6 in the second position II is about 10 N.

The coupling shroud 6 bears against a distal end of the needle shroud 3 to allow the needle shroud 3 to be decoupled from the housing 2 or allow the auto-injector 1 to switch from a second state to a first state, so that the needle shroud 3 may be moved to the safe position PS by the action of the further relaxing drive means 8. As the biasing force exerted onto the needle shroud 3 by the drive means 8 may be relatively large and could even bruise the patient, the rotating collar 14 is arranged within the housing 2 to partially absorb the excess energy of the drive means 8 and slow down the proximal movement of the needle shroud 3 by generating friction.

Figure 5:
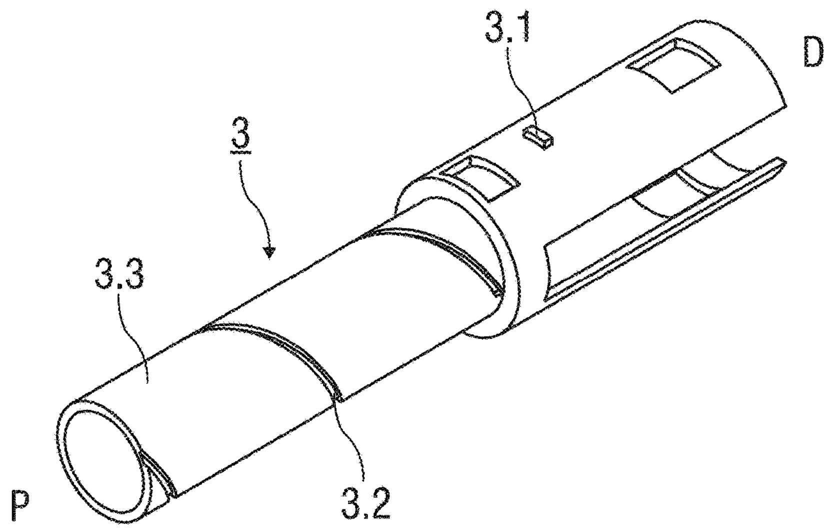
FIG. 5 is an isometric view of a needle shroud.
Figure 6A:
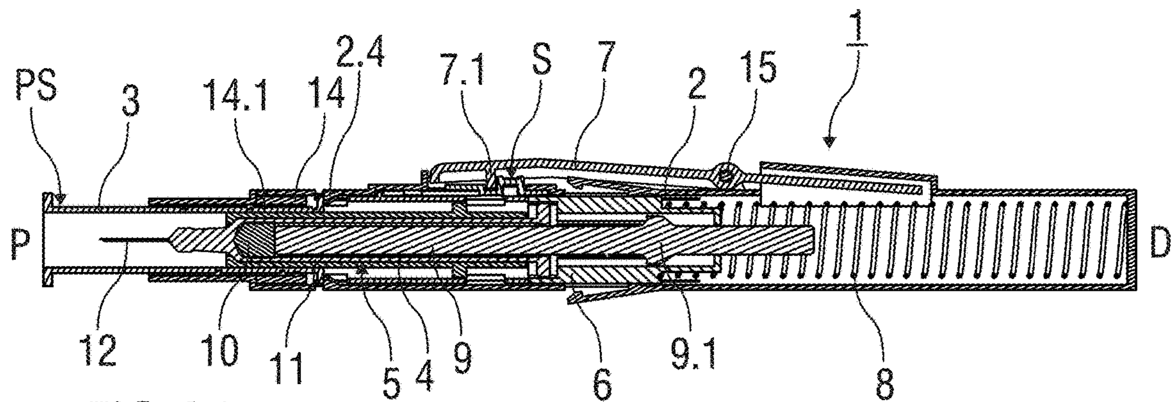
FIGS. 6A and 6B are two different sectional views of the auto-injector according to the first embodiment after an injection has been performed.

FIG. 5 shows an isometric view of the needle shroud 3. A helical recess 3.2 is formed into a tubular proximal section 3.3 of the needle shroud 3. The proximal section 3.3 of the needle shroud 3 is inserted into the annular rotating collar 14, wherein a pin 14.1 formed to an inner surface of the rotating collar 14 protrudes into the helical recess 3.2 as shown in FIG. 6A. The linear translatory movement of needle shroud 3 towards the safe position PS thus causes the rotating collar 14 to rotate within the housing 2 around the axis of the auto-injector 1.

Figure 6B:
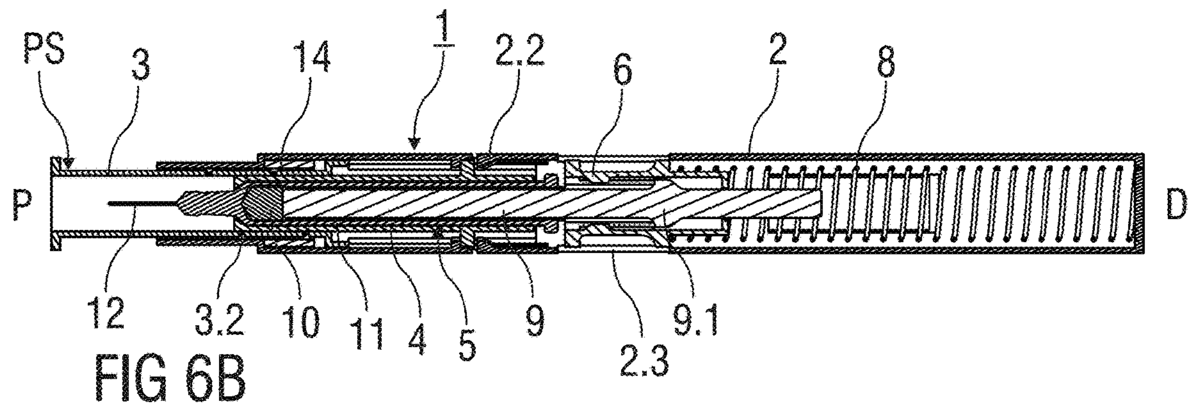

FIGS. 6A and 6B show two different sectional views of the auto-injector 1 according to the first embodiment of the invention after the injection has been performed. The needle shroud 3 is permanently locked to the safe position PS by a second clip connection 2.4 formed into the housing 2. The needle shroud 3 surrounds the injection needle 12 and extends a suitable distance proximally beyond the needle tip to avoid accidental needle stick injuries after the auto-injector 1 has been used.

Figure 7A:
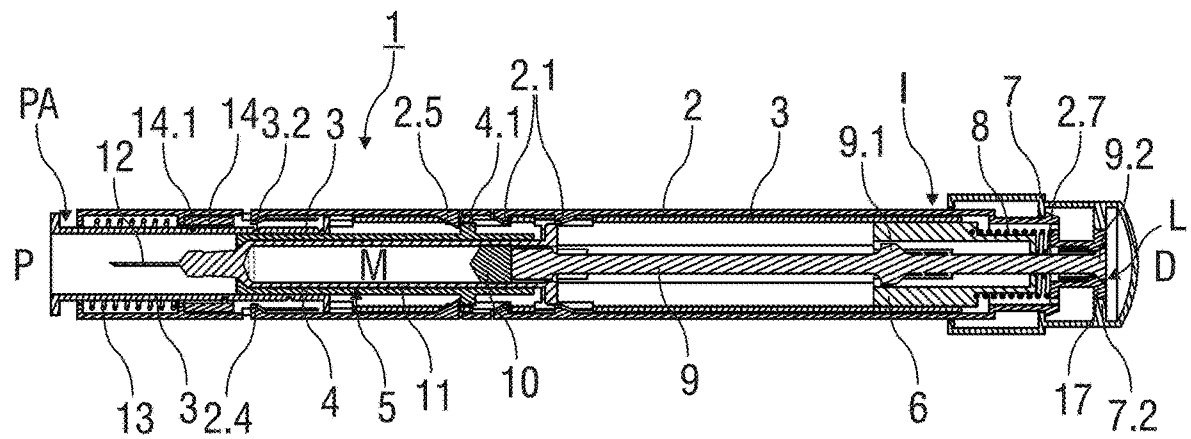
FIGS. 7A and 7B are two different sectional views of an auto-injector according to a second embodiment of the invention.
Figure 7B:
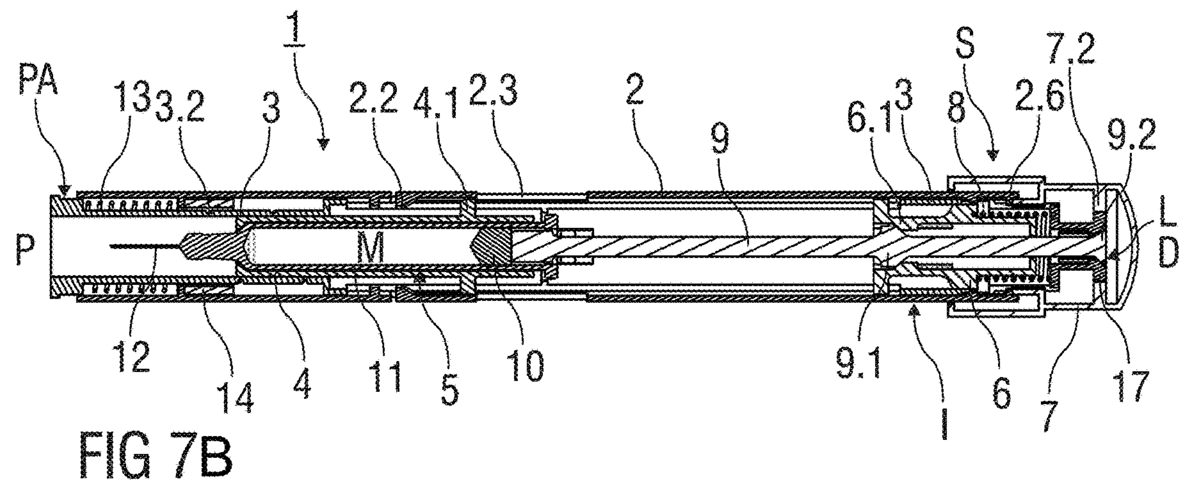

FIGS. 7A and 7B show two different sectional views of an auto-injector 1 according to a second embodiment of the invention before the injection. The sectional plane shown in FIG. 7A (e.g. a first cross-sectional plane) is oriented perpendicularly to the sectional plane (e.g., a second cross-sectional plane) shown in FIG. 7B.

The needle shroud 3 of the auto-injector 1 according to the second embodiment substantially extends over the axial length of the housing 2. Before the injection, the needle shroud 3 is mounted to the housing 2 by the retaining protrusions 2.1 that protrude into orifices formed into a lateral side of the needle shroud 3. The orifices comprise a longitudinal length that allows the needle shroud 3 to be slid from the advanced position PA to the retracted position PR.

A retaining catch 2.5 is formed to an inner surface of the housing 2 and protrudes through an opening formed into the needle shroud 3 to releasably mount the syringe retainer 4 retaining the pre-filled syringe 5. The retaining catch 2.5 comprises a bevelled ramp and is deflectable in a radial outward direction. The retaining catch 2.5 latches to the outward protrusion 4.1 formed to the outer surface of the syringe retainer 4 when the needle shroud 3 is in the advanced position PA The needle shroud 3 abuts against the bevelled ramp of the retaining catch 2.5 when the needle shroud 3 is moved from the advanced position PA in the distal direction D, whereby the retaining catch 2.5 is deflected in a radial outward direction and disengages the outward protrusion 4.1, so that the syringe retainer 4 may be moved in the proximal direction P.

Figure 8:
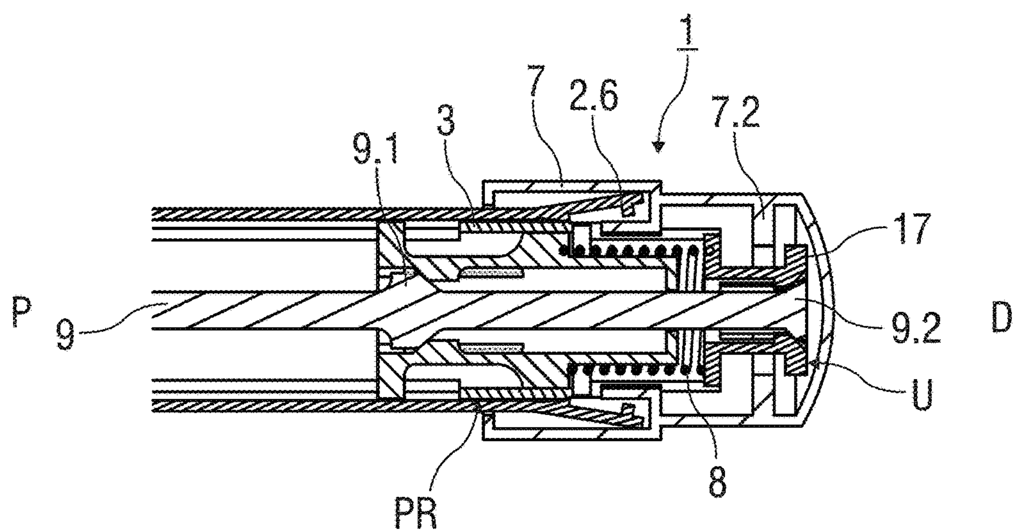
FIG. 8 is a sectional view of a distal end section of the auto-injector according to the second embodiment of the invention.

The release element 7, shown in more detail in FIG. 8, is arranged as a push button and mounted to a distal end of the housing 2. The release element 7 may be pushed in the proximal direction P to release the drive means 8 when the needle shroud 3 is in the retracted position PR, whereas the release element 7 and thus the release of the drive means 8 is blocked when the needle shroud 7 is in the advanced position PA.

According to the second embodiment of the invention, the safety means S that prevent the early release of the drive means 8 comprises clips 2.6 that may deflect in a radial outward direction and a bushing 17 locking the plunger 9 before use of the auto-injector 1.

Before the auto-injector 1 is used, the clips 2.6 formed to the housing 8 latch to the release element 7. (See FIG. 7B) The clips 2.6 block the movement of the release element 7 in the proximal direction P, so that a manual actuation of the release element 7 is prevented as long as the needle shroud 3 is in the advanced position PA. A distal movement of the release element 7 is blocked by a first detent 2.7 engaging an inner surface of the release element 7.

The clip 2.6 comprises a ramp that the needle shroud 3 engages when pushed distally from the advanced position PA to the retracted position PR, whereby the clip 2.6 is deflected radially outwards to disengage the needle shroud 3. The release element 7 may be pushed in the proximal direction P when the needle shroud 3 is in the retracted position PR.

The plunger 9 comprises a distal end 9.2 of increased diameter that is retained in the bushing 17 firmly attached to a distal end of the housing 2. The bushing 17 comprises an inner surface corresponding to the distal end 9.2 of the plunger 9 that engages the distal end 9.2 in a locked position L to lock the plunger 9 and the coupling shroud 6 coupled thereto to the housing 2 before use of the auto-injector 1. An outer surface 9.3 at the distal end 9.2 of the plunger 9 is configured to releasably hold the plunger 9 in an initial position relative to the syringe 5 (e.g., by engagement with the bushing 17) prior to the auto-injector 1 dispensing of the medicament from the syringe 5. The bushing 17 abuts radially against an annular inner collar 7.2 of the release element 7 in the locked position L shown in FIGS. 7A and 7B. A radial outward deflection of the bushing 17 releasing the plunger 9 is thus prevented.

FIG. 8 shows a sectional view of a distal end section of the auto-injector 1 according to the second embodiment of the invention. The needle shroud 3 is located in the retracted position PR and the release element 7 is pushed in the proximal direction P, so that the bushing 17 disengages the annular inner collar 7.2 of the release element 7. The bushing 17 is positioned in an unlocked position U and may deflect outwardly to release the plunger 9.

Furthermore, the bushing 17 acts as a counter bearing for the drive means 8 bearing against the bushing 17 in the distal direction D.

Figure 9A:
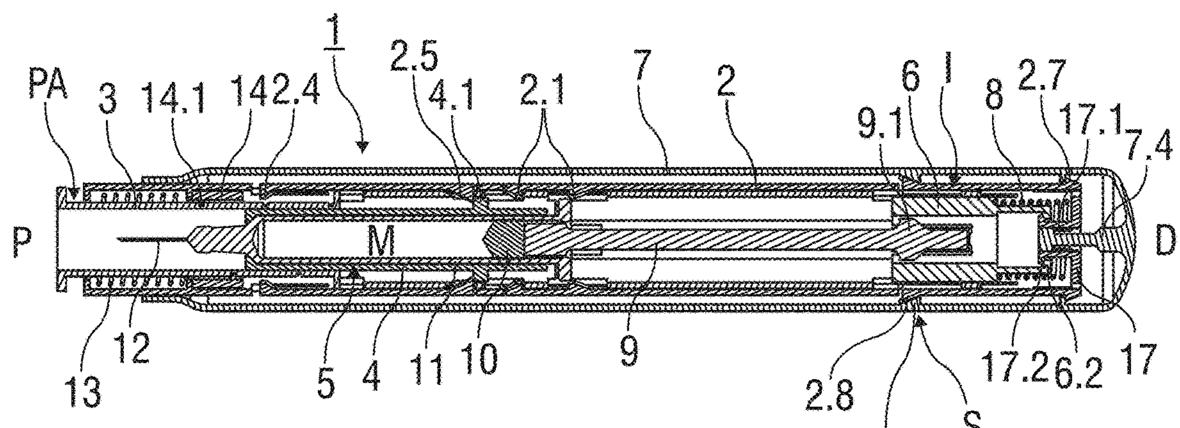
FIGS. 9A and 9B are two different sectional views of an auto-injector according to a third embodiment of the invention.
Figure 9B:
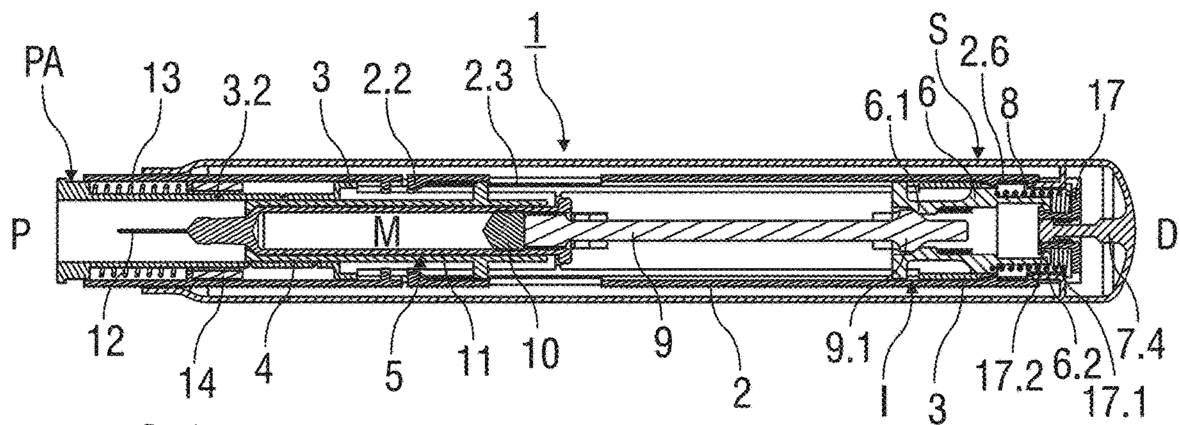

FIGS. 9A and 9B show two different sectional views of an auto-injector 1 according to a third embodiment of the invention, wherein the release element 7 is arranged as an outer sleeve extending over a substantial length of the auto-injector 1.

According to the third embodiment of the invention, the safety means S that prevent the early release of the drive means 8 comprise clips 2.6, second and third detents 2.8, 7.3, a locking catch 6.2 formed to the coupling shroud 6 and the bushing 17 that comprises an inner sleeve 17.1 receiving a lug 7.4, wherein the locking catch 6.2 latches to a collar 17.2 of the inner sleeve 17.1.

The release element 7 of the third embodiment is gripped by a user to perform the injection. When the needle shroud 3 is in the advanced position PA, the proximal displacement of the release element 7 is blocked by the clips 2.6 in a similar manner as in the second embodiment described herein above.

Additionally, the release element is releasably retained in position before the injection by the second and the third detents 2.8, 7.3 respectively formed to an outer surface of the housing 2 and to an inner surface of the release element 7, wherein the second and third detents 2.8, 7.3 comprise correspondingly shaped ramps facing each other.

The bushing 17 of the third embodiment comprises the inner sleeve 17.1 that receives the lug 7.4 formed to an inner surface of the release element 7. A proximal end of the lug 7.4 snugly fits in the central aperture of the inner sleeve 17.1, so that an inward deflection of the inner sleeve 17.1 is prevented.

The inner sleeve 17.1 comprises a collar 17.2. An inwardly protruding locking catch 6.2 of the coupling shroud 6 latches to the collar 17.2 before use of the auto-injector 1 to releasably retain the coupling shroud 6 in the first position I.

Figure 10:
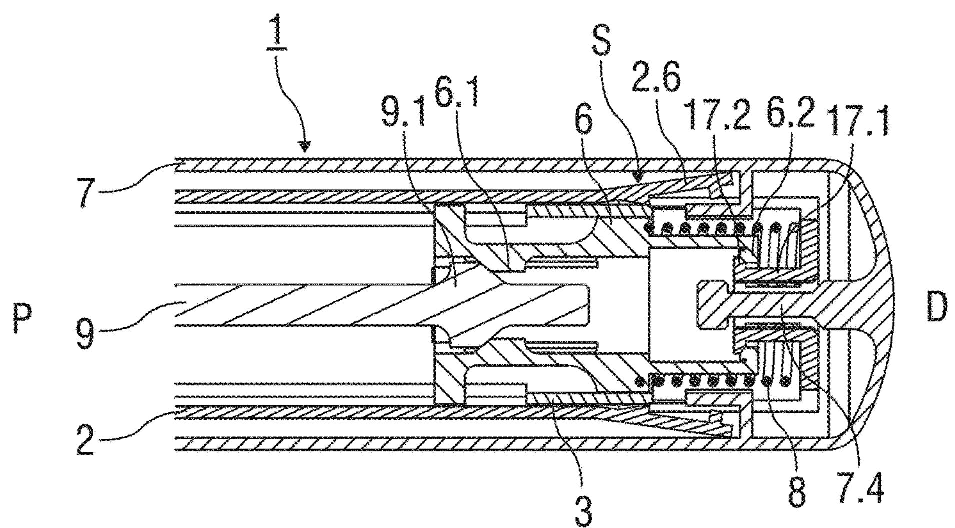
FIG. 10 is a sectional view of a distal end section of the auto-injector according to the third embodiment of the invention.

FIG. 10 shows a sectional view of a distal end section of the auto-injector 1 according to the third embodiment of the invention. The release element 7 is actuated and moved in the proximal direction P. The proximal end of the lug 7.4 disengages the inner sleeve 17.1 of the bushing 17, so that the inner sleeve 17.1 may bend radially inwards, whereby the locking catch 6.2 disengages the collar 17.2 and releases the coupling shroud 8 and the drive means 8.

The invention claimed is:

1. An auto-injector comprising:

a housing;

a syringe retainer disposed in the bousing, the syringe retainer configured to at least partially hold a syringe containing a medicament;

a sleeve disposed within the housing, the sleeve configured to axially move from a first position in which a needle of the syringe extends from a proximal end of the auto-injector to a safe position in which the needle of the syringe does not extend from the proximal end of the auto-injector, wherein the auto-injector is configured such that a clip locks the sleeve in the safe position once the sleeve has reached the safe position;

a plunger rod disposed within the housing, the plunger rod comprising a shoulder, a proximally-extending portion extending proximally from the shoulder to a proximal end of the plunger rod, and a distally-extending portion extending distally from the shoulder to a distal end of the plunger rod, wherein an axial length of the proximally-extending portion of the plunger rod is greater than an axial length of the distally-extending portion of the plunger rod, the proximal end of the plunger rod is configured to engage and push a stopper within the syringe to dispense the medicament from the syringe, and an outer surface at the distal end of the plunger rod is configured to releasably hold the plunger rod in an initial position relative to the syringe prior to the auto-injector dispensing of the medicament from the syringe;

a decoupling member disposed within the housing, located radially outward of the plunger rod, and configured to allow the sleeve to be decoupled from the housing, the decoupling member having an axial length that is less than the axial length of the proximally-extending portion of the plunger rod, wherein the auto-injector is configured such that when viewed in a first cross-sectional plane before and after medicament delivery, (i) the decoupling member is visible, and (ii) the proximally-extending portion of the plunger rod is visible and symmetric about a central axis of the housing;

an annular rotatable collar axially fixed within the housing and configured to rotate about the central axis of the housing relative to the sleeve to increase an amount of time between (i) the decoupling member allowing the sleeve to be decoupled from the housing and (ii) the sleeve arriving in the safe position; and a spring disposed within the housing and distally of the annular rotatable collar, the spring configured to provide a force to rotate the annular rotatable collar relative to the sleeve after the sleeve has decoupled from the housing; and a release element configured to allow the plunger rod to be released from being held in the initial position upon being depressed by a user such that the proximal end of the plunger rod proximally pushes the stopper within the syringe to dispense the medicament from the syringe when the syringe is disposed in the housing.

2. The auto-injector of claim 1, wherein the auto-injector is configured such that the decoupling member and the plunger rod move together proximally relative to the sleeve.

3. The auto-injector of claim 2, wherein the auto-injector is configured such that the decoupling member and the plunger rod move together proximally relative to the sleeve from a distal position in which an entirety of the decoupling member is distal to a distal flange of the syringe.

4. The auto-injector of claim 2, wherein the auto-injector is configured such that the decoupling member and the plunger rod move together proximally relative to the sleeve until the decoupling member engages and deflects an elastically-supported retaining protrusion to release the elastically-supported retaining protrusion out of engagement with the sleeve to decouple the sleeve from the housing.

5. The auto-injector of claim 1, wherein the auto-injector is configured such that when viewed in a second cross-sectional plane perpendicular to the first cross-sectional plane, the decoupling member is visible.

6. The auto-injector of claim 1, wherein the auto-injector is configured such that when viewed in a second cross-sectional plane perpendicular to the first cross-sectional plane, the proximally-extending portion of the plunger rod is visible and symmetric about the central axis of the housing.

7. The auto-injector of claim 6, wherein the auto-injector is configured such that when viewed in the second cross-sectional plane, the distally-extending portion of the plunger rod is visible and symmetric about the central axis of the housing.

8. The auto-injector of claim 1, wherein the auto-injector is configured such that when viewed in the first cross-sectional plane, the distally-extending portion of the plunger rod is visible and symmetric about the central axis of the housing.

9. The auto-injector of claim 1, wherein the proximally-extending portion of the plunger rod comprises a first proximal portion and a second proximal portion, the second proximal portion being proximal to the first proximal portion, and the second proximal portion having a larger outer dimension compared to the first proximal portion.

10. The auto-injector of claim 9, wherein an axial length of the first proximal portion of the plunger rod is greater than an axial length of the second proximal portion of the plunger rod.

11. The auto-injector of claim 10, wherein the axial length of the distally-extending portion of the plunger rod is greater than the axial length of the second proximal portion of the plunger rod.

12. The auto-injector of claim 1, wherein an outer diameter of the distally-extending portion of the plunger rod is constant along a majority of the axial length of the distally-extending portion.

13. The auto-injector of claim 1, wherein the decoupling member and rod are distinct components of the auto-injector.

14. An auto-injector comprising:

a housing;

a syringe retainer disposed in the housing, the syringe retainer configured to at least partially hold a syringe containing a medicament;

a plunger rod disposed within the housing, the plunger rod comprising a shoulder, a proximally-extending portion extending proximally from the shoulder to a proximal end of the plunger rod, and a distally-extending portion extending distally from the shoulder to a distal end of the plunger rod, wherein an axial length of the proximally-extending portion of the plunger rod is greater than an axial length of the distally-extending portion of the plunger rod, the proximal end of the plunger rod is configured to engage and push a stopper within the syringe to dispense the medicament from the syringe, and an outer surface at the distal end of the plunger rod is configured to releasably hold the plunger rod in an initial position relative to the syringe prior to the auto-injector dispensing of the medicament from the syringe;

a decoupling member disposed within the housing, the decoupling member located radially outward of the plunger rod, the decoupling member having an axial length that is less than the axial length of the proximally-extending portion of the plunger rod, wherein the auto-injector is configured such that when viewed in a first cross-sectional plane before and after medicament delivery, (i) the decoupling member is visible, and (ii) the proximally-extending portion of the plunger rod is visible and symmetric about a central axis of the housing;

an annular rotatable collar axially fixed within the housing and configured to rotate about the central axis of the housing relative to the housing to increase an amount of time between (i) medicament delivery and (ii) a needle of the syringe being covered after medicament delivery; and a spring disposed within the housing and distally of the annular rotatable collar, the spring configured to provide a force to rotate the annular rotatable collar relative to the housing; and a release element configured to allow the plunger rod to be released from being held in the initial position upon being depressed by a user such that the proximal end of the plunger rod proximally pushes the stopper within the syringe to dispense the medicament from the syringe when the syringe is disposed in the housing.

15. The auto-injector of claim 14, wherein the auto-injector is configured such that the decoupling member and the plunger rod move together proximally relative to the housing.

16. The auto-injector of claim 15, wherein the decoupling member and the plunger rod are distinct components of the auto-injector.

17. The auto-injector of claim 15, wherein the auto-injector is configured such that the decoupling member and the plunger rod move together proximally relative to the housing from a distal position in which an entirety of the decoupling member is distal to a distal flange of the syringe.

18. The auto-injector of claim 14, wherein the auto-injector is configured such that when viewed in a second cross-sectional plane perpendicular to the first cross-sectional plane, the decoupling member is visible.

19. The auto-injector of claim 14, wherein the auto-injector is configured such that when viewed in the first cross-sectional plane, the distally-extending portion of the plunger rod is visible and symmetric about the central axis of the housing.

20. An auto-injector comprising:

a housing;

a syringe retainer configured to at least partially hold a syringe containing a medicament;

a sleeve configured to axially move to a safe position in which a needle of the syringe is circumferentially covered;

a plunger rod comprising a shoulder, a proximally-extending portion extending proximally from the shoulder, and a distally-extending portion extending distally from the shoulder, the proximally-extending portion comprising a first axially-extending portion and a second axially-extending portion, the second axially-extending portion being proximal to the first axially-extending portion, the second axially-extending portion having a larger outer dimension compared to the first axially-extending portion, and an axial length of the proximally-extending portion of the plunger rod being greater than an axial length of the distally-extending portion of the plunger rod;

a decoupling member located radially outward of the plunger rod and being configured to allow the sleeve to be decoupled from the housing, wherein the auto-injector is configured such that the decoupling member and the plunger rod move together proximally relative to the sleeve until the sleeve begins to move toward the safe position, and the auto-injector is configured such that when viewed in a first cross-sectional plane, the decoupling member is visible, the first axially-extending portion of the plunger rod is visible and symmetric about a central axis of the housing, and the second axially-extending portion of the plunger rod is visible and symmetric about the central axis of the housing;

an annular rotatable collar axially fixed within the housing and configured to rotate about the central axis of the housing relative to the sleeve to increase an amount of time it takes for the sleeve to arrive in the safe position; and a spring configured to provide a force to rotate the annular rotatable collar relative to the sleeve.

21. The auto-injector of claim 20, comprising a release element configured to release the plunger rod to dispense the medicament from the syringe when the syringe is disposed in the syringe retainer, wherein a distal end of the release element is configured to be depressed proximally relative to the housing to release the plunger rod.

22. The auto-injector of claim 20, wherein the auto-injector is configured such that a clip locks the sleeve in the safe position once the sleeve has reached the safe position to prevent reuse of the auto-injector.

23. The auto-injector of claim 20, wherein the auto-injector is configured such that when viewed in a second cross-sectional plane perpendicular to the first cross-sectional plane, the first axially-extending portion of the plunger rod is visible and symmetric about the central axis of the housing, and the second axially-extending portion of the plunger rod is visible and symmetric about the central axis of the housing.

24. The auto-injector of claim 20, wherein the syringe is disposed in the housing.

25. An auto-injector comprising:

a housing for a syringe containing a medicament;

a sleeve configured to axially slide relative to the housing when the auto-injector is in a first state, and be slidably locked relative to the housing when the auto-injector is in a second state; and a plunger rod comprising a shoulder, a proximally-extending portion extending proximally from the shoulder, and a distally-extending portion extending distally from the shoulder, an axial length of the proximally-extending portion of the plunger rod being greater than an axial length of the distally-extending portion of the plunger rod;

a decoupling member located radially outward of the plunger rod that is configured to allow the auto-injector to switch from the second state to the first state, the decoupling member having an axial length that is less than the axial length of the proximally-extending portion of the plunger rod, wherein the auto-injector is configured such that when viewed in a first cross-sectional plane, the decoupling member is visible, and the proximally-extending portion of the plunger rod is visible and symmetric about a central axis of the housing;

an annular rotatable collar axially fixed within the housing and configured to rotate about the central axis of the housing relative to the sleeve to increase an amount of time it takes for the sleeve to arrive in the second state after being in the first state; and a spring configured to provide a force to rotate the annular rotatable collar relative to the sleeve.

26. The auto-injector of claim 25, wherein the proximally-extending and distally-extending portions of the plunger rod are centered on the central axis of the housing.

27. The auto-injector of claim 25, wherein the decoupling member and the plunger rod are distinct components of the auto-injector.

28. The auto-injector of claim 25, wherein an axial length of a first portion of the proximally-extending portion of the plunger rod is greater than an axial length of a second portion of the proximally-extending portion of the plunger rod.

29. The auto-injector of claim 28, wherein the axial length of the proximally-extending portion of the plunger rod is greater than the axial length of the second portion of the plunger rod.

30. The auto-injector of claim 25, wherein the syringe is disposed in the housing.

* * * * *

UNITED STATES PATENT AND TRADEMARK OFFICE

CERTIFICATE OF CORRECTION

PATENT NO. : 12,409,275 B2
APPLICATION NO. : 19/024657
DATED : September 9, 2025
INVENTOR(S) : Yannick Hourmand et al.

It is certified that error appears in the above-identified patent and that said Letters Patent is hereby corrected as shown below:

In the Claims

Column 11, Line 15, Claim 1, delete “bousing,” and insert -- housing --

Column 11, Line 59, Claim 1, after “position;” delete “and”

Column 13, Lines 28-29, Claim 14, after “delivery;” delete “and”

Column 14, Line 60, Claim 25, after “state;” delete “and”

Signed and Sealed this
Twenty-first Day of October, 2025

John A. Squires
*Director of the United States Patent and Trademark Office*